(12) United States Patent
Zhang et al.

(10) Patent No.: US 12,399,113 B2
(45) Date of Patent: Aug. 26, 2025

(54) METHOD FOR MONITORING TEMPERATURE-INDUCED DEFORMATION OF COMPONENTS IN INTELLIGENT MOXIBUSTION ROBOT BASED ON INFRARED SPECTROSCOPY

(71) Applicant: Yueyang Hospital of Integrated Traditional Chinese and Western Medicine, Shanghai Univ. of T.C.M., Shanghai (CN)

(72) Inventors: Chunyan Zhang, Shanghai (CN); Chuting Wu, Shanghai (CN); Yuan Gao, Shanghai (CN); Yunyi Li, Shanghai (CN)

(73) Assignee: Yueyang Hospital of Integrated Traditional Chinese and Western Medicine, Shanghai Univ. of T.C.M., Shanghai (CN)

( * ) Notice: Subject to any disclaimer, the term of this patent is extended or adjusted under 35 U.S.C. 154(b) by 0 days.

(21) Appl. No.: 19/173,729

(22) Filed: Apr. 8, 2025

(65) Prior Publication Data

US 2025/0251341 A1  Aug. 7, 2025

Related U.S. Application Data

(63) Continuation of application No. PCT/CN2024/092540, filed on May 11, 2024.

(30) Foreign Application Priority Data

Apr. 8, 2024  (CN) .......................... 202410411263.5

(51) Int. Cl.
*G01N 21/35*  (2014.01)
*A61B 34/30*  (2016.01)
*A61B 90/00*  (2016.01)

(52) U.S. Cl.
CPC ............. *G01N 21/35* (2013.01); *A61B 34/30* (2016.02); *A61B 90/06* (2016.02); *A61B 90/37* (2016.02);
(Continued)

(58) Field of Classification Search
CPC ........... G01N 21/35; G01N 2021/3595; A61B 34/30; A61B 90/06; A61B 90/37; A61B 2090/376
See application file for complete search history.

(56) References Cited

FOREIGN PATENT DOCUMENTS

CN          108169156 A      6/2018
CN          112700437 A      4/2021
(Continued)

OTHER PUBLICATIONS

Zheng FANG et al., "Study on the Estimation Algorithm of the Temperature Based on Mid-Wave Infrared Remote Sensing", Spectroscopy and Spectral Analysis, vol. 36, No. 4, Apr. 15, 2016, pp. 960-966.

*Primary Examiner* — David P Porta
*Assistant Examiner* — Fani Polyzos Boosalis

(57) ABSTRACT

A method for monitoring temperature-induced deformation of components in an intelligent moxibustion robot based on infrared spectroscopy includes the following steps. Infrared spectral images and frequency spectra of a target component of the intelligent moxibustion robot at different detection points are acquired. Motion influence confidence factors for each detection position are constructed based on frequency differences between peaks and troughs in the frequency spectrum. The box-counting method is used to obtain scale-relationship graphs of infrared spectra for all detection positions. The overall light absorption difference index of the target component is determined according to the scale-relationship graphs. By combining the overall light absorp- (Continued)

tion difference index with motion influence confidence factors, local outlier factors (LOF) for each detection position in the thermal data sequence are calculated using a LOF anomaly detection algorithm. Finally, a temperature deformation risk of the target component is evaluated based on a thermal alarm threshold.

5 Claims, 3 Drawing Sheets

(52) U.S. Cl.
CPC ............... *A61B 2090/376* (2016.02); *G01N 2021/3595* (2013.01)

(56) References Cited

FOREIGN PATENT DOCUMENTS

| | | | |
|---|---|---|---|
| CN | 113450425 | A | 9/2021 |
| CN | 115561193 | A | 1/2023 |
| CN | 116873156 | A | 10/2023 |
| CN | 117292131 | A | 12/2023 |
| CN | 117490834 | A | 2/2024 |
| CN | 117556714 | A | 2/2024 |
| CN | 117804368 | A | 4/2024 |
| JP | 2001343324 | A | 12/2001 |
| WO | 2018060967 | A1 | 4/2018 |
| WO | WO-2021263083 | A1 * | 12/2021 ......... A61B 1/00167 |

* cited by examiner

Schematic diagram of curve coverage by boxes with an initial side length    Schematic diagram of curve coverage by boxes with a reduced side length

METHOD FOR MONITORING TEMPERATURE-INDUCED DEFORMATION OF COMPONENTS IN INTELLIGENT MOXIBUSTION ROBOT BASED ON INFRARED SPECTROSCOPY

CROSS-REFERENCE TO RELATED APPLICATIONS

This application is a continuation of International Patent Application No. PCT/CN2024/092540, filed on May 11, 2024, which claims the benefit of priority from Chinese Patent Application No. 202410411263.5, filed on Apr. 8, 2024. The content of the aforementioned application, including any intervening amendments thereto, is incorporated herein by reference in its entirety.

TECHNICAL FIELD

This application relates to infrared spectroscopy processing, and more specifically to a method for monitoring temperature-induced deformation of components in an intelligent moxibustion robot based on infrared spectroscopy.

BACKGROUND

The intelligent moxibustion robot integrates traditional moxibustion therapy with modern smart technology, representing an innovative trend that fuses tradition with modernity in the medical field. This device not only provides personalized body conditioning for users, improving therapeutic outcomes, but also utilizes intelligent sensing technology to monitor physiological parameters of users in real time, offering scientifically grounded health recommendations. The automated features of the intelligent moxibustion robot enhance medical efficiency and reduce the workload of healthcare professionals, and also enable patients to perform self-treatment at home. Furthermore, the development of intelligent moxibustion robots promotes the application of traditional Chinese medicine in modern healthcare, making ancient therapies more satisfy contemporary needs while expanding market opportunities in the health industry. Therefore, the intelligent moxibustion robot has significant clinical value and broad commercial prospects, and introduces a new direction for advancements in the medical field.

However, due to factors such as poor design, excessive workload, mechanical failure, or external environmental conditions, certain components of the moxibustion robot may overheat to cause deformation. Unreasonable design and material selection, prolonged high-load operation, or damage-induced malfunctions can lead to abnormal temperature conditions. Infrared spectroscopy plays a crucial role in detecting high-temperature deformation in components of the robot. By measuring the infrared radiation emitted by target components, their surface temperature distribution can be obtained. Nevertheless, since different materials exhibit varying infrared radiation characteristics, discrepancies between the actual infrared radiation properties of the target material and expected values may compromise detection accuracy. Additionally, since the moxibustion robot remains in operation during testing, shadows caused by the movements of the robot in the detection area can interfere with infrared spectral measurements, leading to inaccurate results.

SUMMARY

An objective of the present disclosure is to provide a method for monitoring temperature-induced deformation of components in an intelligent moxibustion robot based on infrared spectroscopy to resolve the technical issued in the prior art.

Technical solutions of the present disclosure are described below.

The present disclosure provides a method for monitoring temperature-induced deformation of components in an intelligent moxibustion robot based on infrared spectroscopy, comprising:

collecting infrared spectral images of a target component of the intelligent moxibustion robot at a plurality of detection points;

obtaining frequency spectra of the infrared spectral images using Fast Fourier Transform (FFT); outputting a plurality of peaks and a plurality of troughs in the frequency spectrum using a second-order difference discrimination method; determining a peak width evaluation value for each of the plurality of peaks based on frequency difference between two troughs adjacent to each of the plurality of peaks; calculating an interference peak discrimination factor for each of the plurality of detection points by combining the peak width evaluation value and an amplitude value of each of the plurality of peaks; constructing a motion influence confidence factor for each of the plurality of detection points using the interference peak discrimination factor and frequency values of the plurality of peaks and the plurality of troughs;

obtaining, using a box-counting method, scale relationship graphs of the infrared spectral images at the plurality of detection point based on distribution of spectral curves under different box sizes; counting the number of outliers in the scale relationship graphs for each of the plurality of detection points; determining an overall light absorption difference index of the target component by analyzing distances among the scale relationship graphs of the plurality of detection points and quantity variance among outliers of the scale relationship graphs; constructing a heat data sequence for the target component at each wavelength; calculating, based on the overall light absorption difference index and the motion influence confidence factor, a local outlier factor (LOF) for each of the plurality of detection points in the heat data sequence using a LOF anomaly detection algorithm; and determining a temperature deformation risk of the target component based on the LOF and a heat alarm threshold;

wherein the peak width evaluation value is determined through steps of:

recording a frequency difference between two troughs adjacent to each of the plurality of peaks as a first difference; and taking a hyperbolic tangent function of a difference between the first difference and a preset frequency range threshold; and applying a ceiling function to the hyperbolic tangent function to configure as the peak width evaluation value; the peak width evaluation value is expressed by:

$$Af_k = \sum_{u=1}^{min(R_1,R_2)} (\lceil \tanh(T_s - A_u^F) \rceil * Df_u);$$

wherein $Af_k$ represents the interference peak discrimination factor at a $k^{th}$ detection point; $R_1$ and $R_2$ represent the number of peaks and the number of troughs in the frequency spectra, respectively; min( ) represents a minimum function; Π represents a ceiling function; tanh( ) represents a hyperbolic tangent function; $T_z$ represents an amplitude threshold; $A_u^F$ represents an amplitude value of a $u^{th}$ peak; and $Df_u$ represents the peak width evaluation value of the $u^{th}$ peak at the $k^{th}$ detection point; the interference peak discrimination factor is expressed by:

$$Ef_k = \begin{cases} \frac{Af_k}{R_1} * \sum_{u=1}^{min(R_1,R_2)} |(G_u - F_u) - (F_u - G_{u-1})|, R_1 > R_2 \\ \frac{Af_k}{R_1} * \sum_{u=1}^{min(R_1,R_2)} |(F_u - G_u) - (G_u - F_{u-1})|, R_1 \leq R_2 \end{cases};$$

wherein $Ef_k$ represents the motion influence confidence factor at the $k^{th}$ detection point; $Af_k$ represents the interference peak discrimination factor at a $k^{th}$ detection point; $R_1$ and $R_2$ represent the number of peaks and the number of troughs in the frequency spectra, respectively; min( ) represents a minimum function; $F_u$ and $F_{u-1}$ represent frequency values of the $u^{th}$ peak and a $(u-1)^{th}$ peak, respectively; and $G_{u-1}$ and $G_u$ represent frequency values of a $(u-1)^{th}$ trough and a $u^{th}$ trough, respectively;

the overall light absorption difference index of the target component is obtained through steps of:
for any two detection points, obtaining a dynamic time warping (DTW) distance between scale relationship graphs of the two detection points; and calculating an absolute difference in the number of outliers between the two scale relationship graphs; and
averaging products of the DTW distance between any two detection points and the absolute difference to obtain a mean value; and configuring the mean value as the overall light absorption difference index of the target component; and the LOF is calculated through steps of:
calculating a negative product of the overall light absorption difference index and the motion influence confidence factor of each detection point in the heat data sequence; and configuring the negative product as an exponent of an exponential function taking a natural constant e as a base; and
obtaining an original local outlier factor for each of the plurality of detection points in the heat data sequence using the LOF anomaly detection algorithm; multiplying a result of the exponential function by the original local outlier factor to determine the LOF for each of the plurality of detection points in the heat data sequence.

In some embodiments, the scale relationship graphs are obtained through steps of:
constructing an initial square box for the infrared spectral images at each of the plurality of detection points by taking a side length of a preset initial box as an initial side length of the initial square box and a center of the infrared spectral images as a center of the initial square box;
gradually decreasing a side length from the initial side length in unit wavelength steps along a horizontal axis to obtain reduced box sizes under different decreasing counts;
tiling square boxes with different reduced sizes in the infrared spectral images, wherein a total tiled area is larger or equal to an area of the initial square box, and tiling positions completely covers the initial square box while intersecting with the initial square box; and counting the number of tiled boxes intersecting with the spectral curve; and
forming the scale relationship graphs of the infrared spectrum for each of the plurality of detection points by arranging the number of the square box in descending order of the side length of the square box.

In an embodiment, the number of outliers in the scale relationship graphs is obtained through steps of:
identifying, using a CURE density clustering algorithm, outliers in the scale relationship graphs at each of the plurality of detection points; and counting the number of the outliers in the scale relationship graphs.

In an embodiment, the heat data sequence is obtained through steps of:
compiling absorbance values of the target component across all wavelengths at each of the plurality of detection points to form the heat data sequence.

In an embodiment, the temperature deformation risk of the target component is determined through steps of:
counting a number of local outlier factors exceeding a preset anomaly threshold for each of the plurality of detection points in the heat data sequences; and
calculating a ratio of the number of the local outlier factors to a total number of detection points on the target component, wherein the temperature deformation risk exists if the ratio is larger than or equal to the heat alarm threshold.

Compared with the prior art, the present disclosure at least has the following beneficial effects.

The present application addresses the interference caused by movement-induced shadows of the moxibustion robot in infrared spectral detection. By employing Fast Fourier Transform (FFT) to construct spectrograms of infrared spectra, interference peak distribution is analyzed based on peak-valley positions and frequency distribution from both horizontal-axis and vertical-axis aspects. The motion influence confidence factor is constructed. Subtle and chaotic fluctuations in spectral entropy caused by persistent shadow variations at joint areas of the robot are captured, effectively reflecting shadow interference in spectral data. Furthermore, to account for reflectance characteristics of surface coatings on the components of the moxibustion robot, an overall light absorption difference index is constructed using a box-counting method, which reflects absorption variations caused by reflective properties across identical structures. The method provided herein integrates the motion influence confidence factor and the light absorption difference index to enhance the local outlier factor (LOF) in the LOF algorithm, which effectively filters out spectral variations induced by shadows and reflective properties, enabling more precise anomaly detection, thereby reaching timely high-temperature alerts for the components while significantly enhancing robustness and detection accuracy of the algorithm.

BRIEF DESCRIPTION OF THE DRAWINGS

To more clearly illustrate the technical solutions in the embodiments of the present disclosure or in the prior art, the drawings required for describing the embodiments or the prior art will be briefly introduced. Obviously, the drawings in the following description are merely some embodiments of the present disclosure. For one of ordinary skill in the art, other drawings may be derived from these illustrations without creative effort.

DETAILED DESCRIPTION OF EMBODIMENTS

To further elaborate on the technical solutions adopted by the present disclosure to achieve intended objectives and effects, a method for monitoring temperature-induced deformation of components in an intelligent moxibustion robot based on infrared spectroscopy is described in detail below with reference to the accompanying drawings and preferred embodiments, including specific implementations, structures, features, and efficacy. It should be noted that different references to "one embodiment" or "another embodiment" in the following description do not necessarily refer to the same embodiment. Furthermore, specific features, structures, or characteristics described in one or more embodiments may be combined in any suitable manner.

Unless otherwise defined, all technical and scientific terms used herein have the same meanings as commonly understood by those skilled in the art.

The method for monitoring temperature-induced deformation of components in an intelligent moxibustion robot based on infrared spectroscopy provided herein will be described in detail below with reference to the accompanying drawings.

Figure 1:
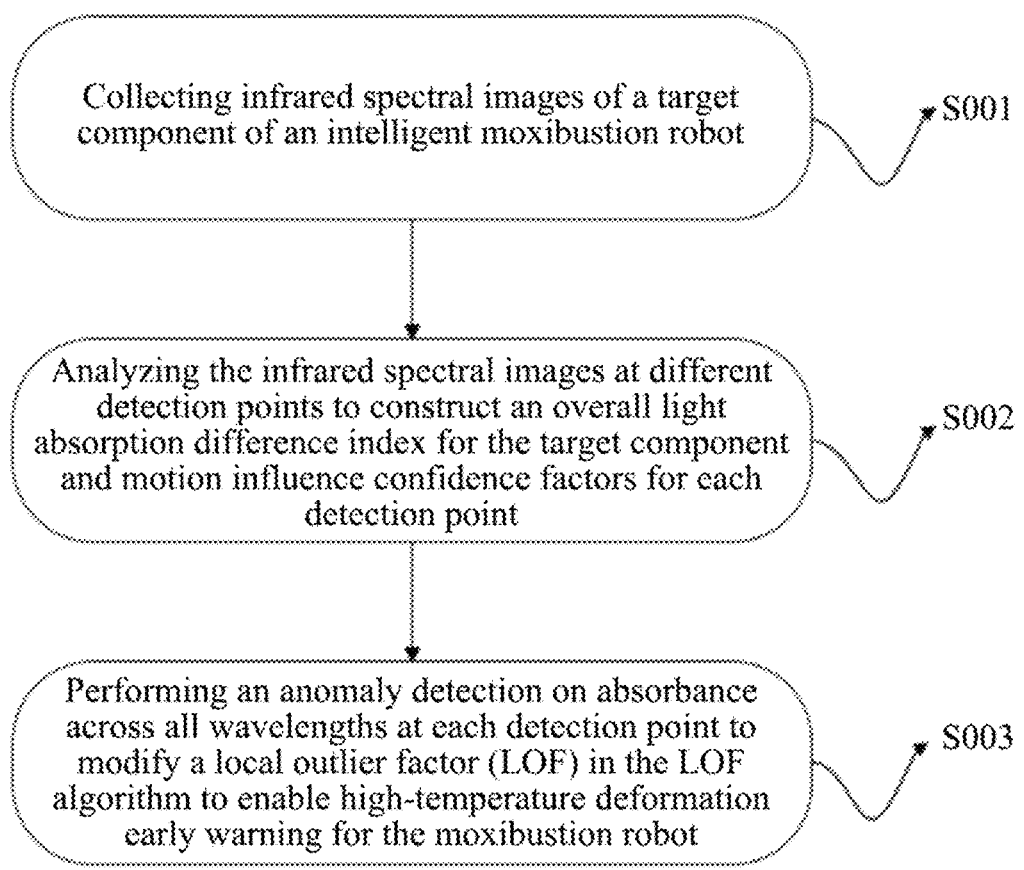
FIG. 1 is a flow chart of a method for monitoring temperature-induced deformation of components in an intelligent moxibustion robot based on infrared spectroscopy according to an embodiment of the present disclosure.

Referring to FIG. 1, a method for monitoring temperature-induced deformation of components in an intelligent moxibustion robot based on infrared spectroscopy is provided, which includes the following steps.

(S001) Infrared spectral images of a target component of the intelligent moxibustion robot are collected.

According to the structural design of the moxibustion robot, the joints and connection points of the moving components of the robot play a critical role in the robotic system. Their design not only determines the movement flexibility, positioning accuracy and load capacity of the robot, but also directly affects the controllability and operational stability of the mechanical structure. A robust and reliable joint system enables the robot to perform complex tasks while ensuring torque transmission and mechanical reliability. Therefore, well-designed joints are key factors in guaranteeing efficient and stable operation of the robot in various working environments, holding significant importance for the development and application of robotic technology. If the joints and connections of the robot undergo deformation due to high temperatures, it will lead to mechanical failure of joint components, causing the robotic arm to malfunction or lose its original precision, thereby affecting the accuracy and control performance of the robot while shortening the service life of the robot. In this embodiment, a joint of the moxibustion robot is selected as a sample for temperature deformation monitoring.

In this embodiment, a scanning infrared spectrometer is used for real-time infrared spectral acquisition of a target component. The infrared spectrometer is aligned with the target component while maintaining a proper measurement distance and angle, enabling real-time capture of infrared radiation data during normal robot operation. The scanning mode of the infrared spectrometer refers to the scanning across the sample surface to obtain infrared spectral data from different locations. In this mode, the spectrometer moves along horizontal or vertical directions, performing point-by-point or line-by-line scanning of the entire sample surface to collect infrared radiation data from various positions. Under the precision limits of the infrared scanner, a total of K detection points are identified on the sample. The infrared spectrometer acquires spectral images for all detection points, where the horizontal axis represents wavelength and the vertical axis indicates absorbance at different wavelengths.

In this case, infrared spectral images for all detection points on the target component of the moxibustion robot can be obtained.

(S002) The infrared spectral images at different detection points are analyzes to construct an overall light absorption difference index for the target component and motion influence confidence factors for each detection point.

Since the infrared scanner performs real-time spectral detection on the moxibustion robot, the monitored joint sample remains in continuous motion, causing persistent variations in joint shadows. The infrared scanner acquires data by detecting reflected or emitted infrared spectra, and fluctuating shadows at the joint may introduce signal instability or distortion, interfering with accurate spectral acquisition. During the continuous motion of the joint, under ideal conditions, the temperature at the joint should rise steadily with continuous motion of the joint. However, compared with the ideal conditions, the actual infrared spectra detected by the infrared scanner is fluctuating due to shadow variations. In this embodiment, a $k^{th}$ detection point is selected as an example for analysis.

For the infrared spectral image at the $k^{th}$ detection point, Fast Fourier Transform (FFT) is performed to convert it into a frequency spectrum, where the FFT is a well-known technique, and thus is not elaborated here. The subtle and chaotic fluctuations caused by joint shadows manifest as interference peaks in the frequency spectrum. In this embodiment, an amplitude threshold $T_z$ is set, and $$T_z = \frac{3}{4} * (A_{k,max} - A_{k,min}),$$

where $A_{k,max}$ and $A_{k,min}$ represent a maximum amplitude and a minimum amplitude in the frequency spectrum, respectively. The frequency spectrum is then processed using a second-order difference discrimination method to output all peaks and troughs, where the second-order difference discrimination method is a well-known technique, and thus is not elaborated here. Assuming that the frequency spectrum contains $R_1$ peaks and $R_2$ troughs. A frequency range threshold $T_p$ is set, and $$T_p = \frac{1}{\min(R_1, R_2) - 1} * \sum_{u=1}^{\min(R_1, R_2)} |F_u - G_u|,$$

where $F_u$ represents a frequency value of the $u^{th}$ peak, and $G_u$ represents a frequency value of the $u^{th}$ trough, that is, $T_p$ represents a mean absolute of a frequency difference between a peak and a trough adjacent thereto. The motion influence confidence factor $Ef_k$ at the $k^{th}$ detection point is then constructed as:

$$Ef_k = \begin{cases} \dfrac{Af_k}{R_1} * \sum_{u=1}^{min(R_1,R_2)} |(G_u - F_u) - (F_u - G_{u-1})|, & R_1 > R_2 \\ \dfrac{Af_k}{R_1} * \sum_{u=1}^{min(R_1,R_2)} |(F_u - G_u) - (G_u - F_{u-1})|, & R_1 \le R_2 \end{cases};$$

$$Af_k = \sum_{u=1}^{min(R_1,R_2)} (\lceil \tanh(T_s - A_u^F) \rceil * Df_u); \text{ and}$$

$$Df_u = \begin{cases} \lceil \tanh((G_u - G_{u-1}) - T_p) \rceil, & R_1 > R_2 \\ \lceil \tanh((G_{u+1} - G_u) - T_p) \rceil, & R_1 \le R_2 \end{cases};$$

where $Ef_k$ represents the motion influence confidence factor at the $k^{th}$ detection point, indicating the impact of joint shadow variations on infrared spectra during moxibustion robot operation; $Af_k$ represents the interference peak discrimination factor at a $k^{th}$ detection point; $R_1$ and $R_2$ represent the number of peaks and the number of troughs in the frequency spectra, respectively; min( ) represents a minimum function; $F_u$ and $F_{u-1}$ represent frequency values of the $u^{th}$ peak and the $(u-1)^{th}$ peak, respectively; and $G_{u-1}$, $G_u$ and $G_{u+1}$ represent frequency values of the $(u-1)^{th}$ trough, the $u^{th}$ trough and the $(u+1)^{th}$ trough, respectively; tanh( ) represents a hyperbolic tangent function; $T_z$ represents an amplitude threshold; $A_u^F$ represents an amplitude value of the $u^{th}$ peak; $Df_u$ represents the peak width evaluation value of the $u^{th}$ peak at the $k^{th}$ detection point; $T_p$ represents a frequency range threshold; ⌈ ⌉ represents a ceiling function; and u represents an index of a summation function.

It should be noted that due to the uncertainty in the number of peaks and troughs in the frequency spectrum, a judgment function is introduced to distinguish and calculate the two troughs adjacent to the $u^{th}$ peak. In the calculation of the motion influence confidence factor $Ef_k$, the interference peak discriminant factor $Af_k$ at the $k^{th}$ detection point is used to quantify all interference peaks. When $T_s > A_u^F$, i.e., the amplitude of the $u^{th}$ peak is less than the threshold, it indicates that the amplitude of the $u^{th}$ peak is below the average level of peak amplitudes, signifying that the amplitude of the peak falls within the range of interference peaks. In this case, the value of $[\tanh(T_z - A_u^F)]$ is set to 1; otherwise, it is 0. The peak width evaluation value $Df_u$ for the $u^{th}$ peak at the $k^{th}$ detection point determines whether the peak is an interference peak by evaluating the width of the $u^{th}$ peak. The frequency difference between the two adjacent troughs of the $u^{th}$ peak is calculated and compared to the frequency range threshold. If the difference between the frequency difference and the frequency range threshold exceeds the threshold, the value obtained after applying the hyperbolic tangent function and the ceiling function is 1; otherwise, it is 0. In other words, the interference peak discriminant factor $Af_k$ combines the height and width of peaks through concatenation and summation to determine the number of interference peaks, which is divided by the total number of peaks to yield the proportion of interference peaks. A higher value indicates a higher proportion of subtle and chaotic fluctuations caused by shadow variations, leading to a larger $Ef_k$. In the frequency spectrum, primary peaks typically exhibit clear symmetrical shapes, while interference peaks may appear irregular shapes. The irregularity of interference peaks is assessed by the value of $|(G_u - F_u) - (F_u - G_{u-1})|$ through comparing the frequency differences between the $u^{th}$ peak and two troughs adjacent thereto. When the $u^{th}$ peak is symmetrical, the value is 0. As the asymmetry of the $u^{th}$ peak increases, the value grows larger, reflecting greater irregularity of the interference peak. This indicates a stronger influence of shadow-induced subtle and chaotic fluctuations on the infrared spectrum, resulting in a larger $Ef_k$.

Since the moxibustion robot is in a state of motion, the coating at its joints exhibits different reflections at different movement positions. The varying positions of the robot may cause changes in the coatings of the joints, thereby affecting the infrared spectral signals and resulting in different peaks or valleys in the spectrum at different locations. During the joint movement of the robot, the temperature changes across the entire joint area tend to be similar, which may be influenced by multiple factors.

Firstly, normal motion is typically accompanied by uniform energy distribution, leading to relatively consistent energy changes across the entire joint region. Secondly, joints of the robot are generally made of metals or other materials with good thermal conductivity, facilitating rapid heat transfer within the joint area and thereby promoting uniform temperature changes. Additionally, well-designed mechanical structures and stable working environments help distribute and evenly transfer heat generated during motion, further maintaining temperature consistency in the joint area. These factors collectively contribute to the overall similarity in temperature variation characteristics of the joints during movement.

However, reflections from the joint coatings can cause differences in the infrared spectra detected at different detection points. Taking the infrared spectrum at the $k^{th}$ detection point as input, when analyzing the spectrum using the box-counting method, the spectrum at the $k^{th}$ detection point is firstly placed into an initial square box. The side length of the initial box must be large enough to fully encompass the range of the spectral data on both the horizontal (wavelength) and vertical (absorbance) axes. To construct a box sequence with progressively smaller sizes, the side length φ is decremented from the initial value in steps corresponding to the unit wavelength on the horizontal axis until the side length reduces to a single unit wavelength. The side length of the initial box is constructed as the side length of the square box, and the center of the infrared spectrum is constructed as the center of the square box. As such, the initial square box of the infrared spectrum is constructed. As the side length decreases, multiple square boxes corresponding to the reduced side lengths are tiled within the initial square box. The total area of the tiled boxes must be greater than or equal to the area of the initial square box, and must completely cover the initial square box. Here, φ is taken from the maximum values of the horizontal and vertical axis data of the spectrum.

Figure 2:
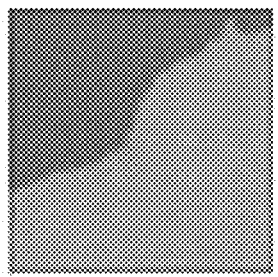
FIG. 2 structurally illustrates arrangement of square boxes according to an embodiment of the present disclosure.
Figure 2:
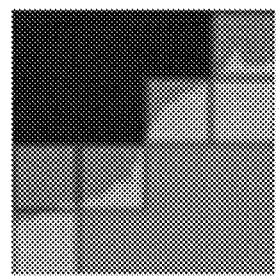

During each iteration of reducing the side length of the box, whether each box contains points on the spectral curve is checked to count the intersection between the boxes and the spectral curve. For each reduced side length and the corresponding number of boxes containing the curve, a coordinate system is established, where the horizontal axis represents the box size and the vertical axis represents the corresponding number of boxes. Finally, by plotting the scale relationship graph of the infrared spectrum at the $k^{th}$ detection point, the changing trend of the box-counting method in analyzing the spectrum can be visualized more intuitively. The box configuration is illustrated in FIG. 2.

The scale relationship graphs of the $k^{th}$ and $l^{th}$ detection points are used as input, the dynamic time warping (DTW) distance between the two scale relationship graphs is calculated. After that, the scale relationship graphs of the $k^{th}$ and $l^{th}$ detection points are input into the clustering using representatives (CURE) density clustering algorithm to output the number of outliers after clustering the above two detection points. The overall light absorption difference index Ps for the joint is constructed as follows:

$$P_S = \frac{1}{K^2} * \sum_{k=1}^{K}\sum_{l=1}^{K}(DTW_{k,l} * |V_k - V_l|);$$

where Ps represents the overall light absorption difference index of the joint, representing the degree of variation in infrared light absorption and reflection caused by factors such as coating or reflection properties; $DTW_{k,l}$ represents a DTW distance between the scale relationship graphs of the $k^{th}$ and $l^{th}$ detection points; $V_k$ and $V_l$ are the numbers of outliers in the scale relationship graphs of the $k^{th}$ and $l^{th}$ detection points, respectively; K represents the total number of detection points on the target component; and k and l represent indices of a summation function.

In the calculation of the overall light absorption difference index, the DTW distance reflects the degree of temporal stretching or compression required for one sequence to achieve optimal alignment with another. A greater distance indicates higher matching difficulty and lower similarity between sequences. Correspondingly, a larger $DTW_{k,l}$ signifies more pronounced differences between the $k^{th}$ and $l^{th}$ detection points, that is, the two detection points on the same joint exhibit increasingly dissimilar infrared spectra, demonstrating a greater spectral variation caused by factors like coating reflectivity, leading to a larger Ps. Simultaneously, in the scale relationship graph, the number of boxes containing spectral curves progressively increases as box size decreases. The presence of outliers in the scale relationship graph indicates irregular and abrupt fluctuations in the infrared spectrum. A higher number of the outlier reflects more intense spectral anomalies. Consequently, a larger $|V_k - V_l|$ represents greater disparity in outliers between the scale relationship graphs of two detection points, that is, the greater significant differences between infrared spectra of the two detection points, the larger PS.

(S003) Anomaly detection is performed on absorbance across all wavelengths at each detection point to modify the local outlier factor (LOF) in the LOF algorithm to enable high-temperature deformation early warning for the moxibustion robot.

Figure 3:
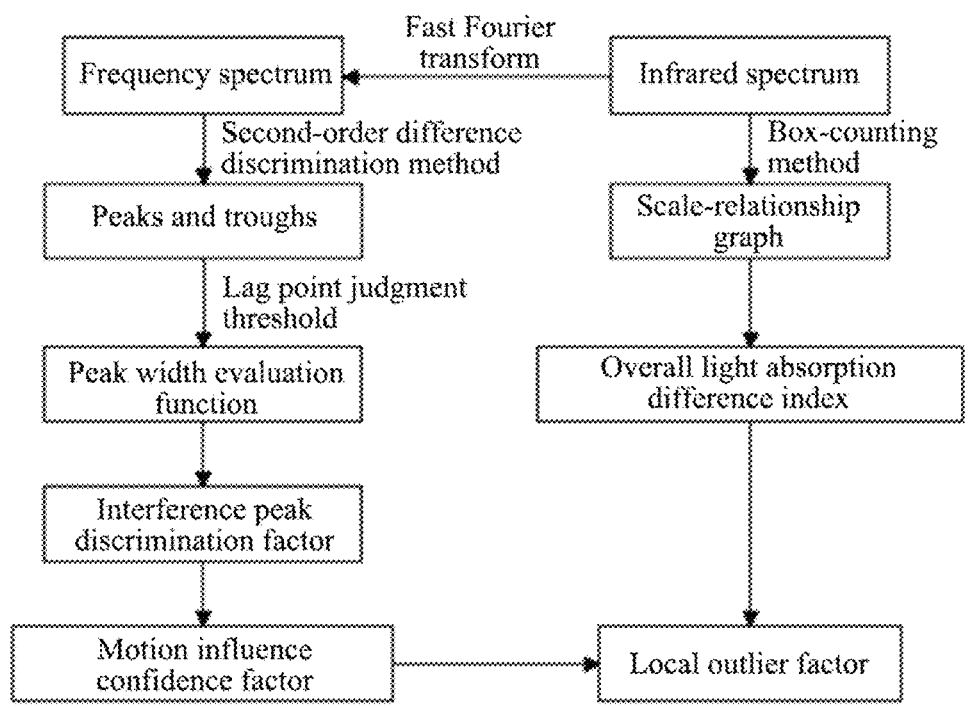
FIG. 3 is a flow chart of constructing s local outlier factor (LOF) according to an embodiment of the present disclosure.

During high-temperature deformation monitoring of the joint, to avoid deformation caused by local heating from friction, absorbance values at all detection points across wavelengths are synchronously recorded to construct a heat data sequence under a specific wavelength. The heat data sequence is used as input, and the LOF anomaly detection algorithm redefines the original local outlier factor for the $k^{th}$ detection point as follows:

$$LOF_{k,new} = e^{-EF_k vPs} * LOF_k;$$

where $LOF_{k,new}$ represents the local outlier factor for the $k^{th}$ detection point; $EF_k$ represents the motion influence confidence factor for the $k^{th}$ detection point; Ps represents the overall light absorption difference index of the joint; and $LOF_k$ represents an original local outlier factor for the $k^{th}$ detection point in the heat data sequence calculated by using the conventional LOF anomaly detection algorithm. The flowchart for constructing the local outlier factor indicator is shown in FIG. 3. The LOF anomaly detection algorithm is a well-known technique and will not be elaborated here.

When the motion influence confidence factor for the $k^{th}$ detection point is larger, it indicates a greater interference in the absorbance detected by the infrared spectrometer due to shadows caused by the movement of the moxibustion robot. To mitigate the influence of shadows, a lower anomaly confidence level is assigned to this detection point, and $LOF_{k,new}$ is accordingly decreased. Meanwhile, Ps reflects the degree of variation in the overall infrared light absorption and reflection of the joint caused by factors such as coating or reflectivity. A higher Ps signifies a greater impact of these factors on the absorbance at the detection point. In this case, the calculation of the overall outlier factor is reduced to exclude the influence of coating or reflectivity on the infrared absorption of the joint, and $LOF_{k,new}$ is accordingly decreased.

An anomaly threshold is set. In this embodiment, the anomaly threshold is taken as the standard deviation of the local outlier factors for all detection points in the heat data sequence. The number of local outlier factors exceeding this threshold is then counted. Suppose the heat data sequence contains a total of H local outlier factors that exceed the threshold. A thermal alarm threshold T is set to 0.15. If H/K≥T, it indicates a high risk of thermal deformation at the joint of the detected component, triggering an alarm to alert personnel to pay additional attention to the joint at the detection point. Here, K represents the total number of detection points on the target component.

In summary, the present application addresses the interference caused by movement-induced shadows of the moxibustion robot in infrared spectral detection. By employing Fast Fourier Transform (FFT) to construct spectrograms of infrared spectra, interference peak distribution is analyzed based on peak-valley positions and frequency distribution from both horizontal-axis and vertical-axis aspects. The motion influence confidence factor is constructed. Subtle and chaotic fluctuations in spectral entropy caused by persistent shadow variations at joint areas of the robot are captured, effectively reflecting shadow interference in spectral data. Furthermore, to account for reflectance characteristics of surface coatings on the components of the moxibustion robot, an overall light absorption difference index is constructed using a box-counting method, which reflects absorption variations caused by reflective properties across identical structures. The method provided herein integrates the motion influence confidence factor and the light absorption difference index to enhance the local outlier factor (LOF) in the LOF algorithm, which effectively filters out spectral variations induced by shadows and reflective properties, enabling more precise anomaly detection, thereby reaching timely high-temperature alerts for the components while significantly enhancing robustness and detection accuracy of the algorithm.

It should be noted that the sequence of embodiments described in this application is merely for illustrative purposes and does not reflect any ranking of their merits. The descriptions of specific embodiments in this specification are provided for clarity. Additionally, the processes depicted in the accompanying drawings do not necessarily require the particular order or continuity shown to achieve the desired results. In some implementations, multitasking and parallel processing may be feasible or even advantageous.

Each embodiment in this specification is described in a progressive manner. For identical or similar parts across different embodiments, cross-referencing is sufficient. The emphasis of each embodiment lies in its distinctions from other embodiments.

The above-mentioned embodiments are intended to illustrate the technical solutions of this application, and are not intended to limit the present disclosure. Modifications to the technical solutions described in the preceding embodiments or equivalent replacements of some technical features should not make the essence of the respective technical solutions to deviate from the scope of the technical solutions of the embodiments of this application. All such modifications and replacements shall fall within the protection scope of this application.

What is claimed is:

1. A method for monitoring temperature-induced deformation of components in an intelligent moxibustion robot based on infrared spectroscopy, comprising:

collecting infrared spectral images of a target component of the intelligent moxibustion robot at a plurality of detection points;

obtaining frequency spectra of the infrared spectral images using Fast Fourier Transform (FFT); outputting a plurality of peaks and a plurality of troughs in the frequency spectrum using a second-order difference discrimination method; determining a peak width evaluation value for each of the plurality of peaks based on frequency difference between two troughs adjacent to each of the plurality of peaks; calculating an interference peak discrimination factor for each of the plurality of detection points by combining the peak width evaluation value and an amplitude value of each of the plurality of peaks; constructing a motion influence confidence factor for each of the plurality of detection points using the interference peak discrimination factor and frequency values of the plurality of peaks and the plurality of troughs;

obtaining, using a box-counting method, scale relationship graphs of the infrared spectral images at the plurality of detection point based on distribution of spectral curves under different box sizes; counting the number of outliers in the scale relationship graphs for each of the plurality of detection points; determining an overall light absorption difference index of the target component by analyzing distances among the scale relationship graphs of the plurality of detection points and quantity variance among outliers of the scale relationship graphs; constructing a heat data sequence for the target component at each wavelength; calculating, based on the overall light absorption difference index and the motion influence confidence factor, a local outlier factor (LOF) for each of the plurality of detection points in the heat data sequence using a LOF anomaly detection algorithm; and determining a temperature deformation risk of the target component based on the LOF and a heat alarm threshold;

wherein the peak width evaluation value is determined through steps of:

recording a frequency difference between two troughs adjacent to each of the plurality of peaks as a first difference; and taking a hyperbolic tangent function of a difference between the first difference and a preset frequency range threshold; and applying a ceiling function to the hyperbolic tangent function to configure as the peak width evaluation value; the peak width evaluation value is expressed by:

$$Af_k = \sum_{u=1}^{min(R_1,R_2)} (\lceil \tanh(T_s - A_u^F) \rceil * Df_u);$$

wherein $Af_k$ represents the interference peak discrimination factor at a $k^{th}$ detection point; $R_1$ and $R_2$ represent the number of peaks and the number of troughs in the frequency spectra, respectively; min( ) represents a minimum function; $\lceil \rceil$ represents a ceiling function; tanh( ) represents a hyperbolic tangent function; $T_z$ represents an amplitude threshold; $A_u^F$ represents an amplitude value of a $u^{th}$ peak; and $Df_u$ represents the peak width evaluation value of the $u^{th}$ peak at the $k^{th}$ detection point;

the interference peak discrimination factor is expressed by:

$$Ef_k = \begin{cases} \dfrac{Af_k}{R_1} * \sum_{u=1}^{min(R_1,R_2)} |(G_u - F_u) - (F_u - G_{u-1})|, R_1 > R_2 \\ \dfrac{Af_k}{R_1} * \sum_{u=1}^{min(R_1,R_2)} |(F_u - G_u) - (G_u - F_{u-1})|, R_1 \leq R_2 \end{cases};$$

wherein $Ef_k$ represents the motion influence confidence factor at the $k^{th}$ detection point; $F_u$ and $F_{u-1}$ represent frequency values of the $u^{th}$ peak and a $(u-1)^{th}$ peak, respectively; and $G_{u-1}$ and $G_u$ represent frequency values of a $(u-1)^{th}$ trough and a $u^{th}$ trough, respectively;

the overall light absorption difference index of the target component is obtained through steps of:

for any two detection points, obtaining a dynamic time warping (DTW) distance between scale relationship graphs of the two detection points; and calculating an absolute difference in the number of outliers between the two scale relationship graphs; and averaging products of the DTW distance between any two detection points and the absolute difference to obtain a mean value; and configuring the mean value as the overall light absorption difference index of the target component; and the LOF is calculated through steps of:

calculating a negative product of the overall light absorption difference index and the motion influence confidence factor of each detection point in the heat data sequence; and configuring the negative product as an exponent of an exponential function taking a natural constant e as a base; and obtaining an original local outlier factor for each of the plurality of detection points in the heat data sequence using the LOF anomaly detection algorithm; multiplying a result of the exponential function by the original local outlier factor to determine the LOF for each of the plurality of detection points in the heat data sequence.

2. The method of claim 1, wherein the scale relationship graphs are obtained through steps of:

constructing an initial square box for the infrared spectral images at each of the plurality of detection points by taking a side length of a preset initial box as an initial side length of the initial square box and a center of the infrared spectral images as a center of the initial square box;

gradually decreasing a side length from the initial side length in unit wavelength steps along a horizontal axis to obtain reduced box sizes under different decreasing counts;

tiling square boxes with different reduced sizes in the infrared spectral images, wherein a total tiled area is larger or equal to an area of the initial square box, and tiling positions completely covers the initial square box while intersecting with the initial square box; and counting the number of tiled boxes intersecting with the spectral curve; and forming the scale relationship graphs of the infrared spectrum for each of the plurality of detection points by arranging the number of the square box in descending order of the side length of the square box.

3. The method of claim 1, wherein the number of outliers in the scale relationship graphs is obtained through steps of:

identifying, using a CURE density clustering algorithm, outliers in the scale relationship graphs at each of the plurality of detection points; and counting the number of the outliers in the scale relationship graphs.

4. The method of claim 1, wherein the heat data sequence is obtained through steps of:

compiling absorbance values of the target component across all wavelengths at each of the plurality of detection points to form the heat data sequence.

5. The method of claim 1, wherein the temperature deformation risk of the target component is determined through steps of:

counting a number of local outlier factors exceeding a preset anomaly threshold for each of the plurality of detection points in the heat data sequences; and calculating a ratio of the number of the local outlier factors to a total number of detection points on the target component, wherein the temperature deformation risk exists if the ratio is larger than or equal to the heat alarm threshold.

* * * * *